(12) United States Patent
Dale

(10) Patent No.: US 12,708,257 B2
(45) Date of Patent: Aug. 18, 2026

(54) ENDODONTIC SURGERY TISSUE RETRACTOR DEVICE

(71) Applicant: Joshua Dale, Coeur d'Alene, ID (US)

(72) Inventor: Joshua Dale, Charleston, SC (US)

(73) Assignee: Joshua Dale, Coeur d'Alene, ID (US)

( * ) Notice: Subject to any disclaimer, the term of this patent is extended or adjusted under 35 U.S.C. 154(b) by 161 days.

(21) Appl. No.: 18/616,606

(22) Filed: Mar. 26, 2024

(65) Prior Publication Data

US 2024/0324871 A1 Oct. 3, 2024

Related U.S. Application Data

(60) Provisional application No. 63/493,017, filed on Mar. 30, 2023.

(51) Int. Cl.
*A61B 1/32* (2006.01)
*A61C 5/00* (2017.01)

(52) U.S. Cl.
CPC ................ *A61B 1/32* (2013.01); *A61C 5/007* (2013.01)

(58) Field of Classification Search
CPC .... A61B 1/24; A61B 1/32; A61C 5/80; A61C 5/90; A61C 5/88; A61C 5/007; A61C 5/50; A61C 5/82
USPC ........................................................ 433/140
See application file for complete search history.

(56) References Cited

U.S. PATENT DOCUMENTS

2010/0291503 A1* 11/2010 Shih ...................... A61B 90/16 433/140
2020/0352680 A1* 11/2020 Nguyen .............. A61C 17/092
2024/0156568 A1* 5/2024 Perry ...................... A61C 5/90

* cited by examiner

*Primary Examiner* — Matthew M Nelson
(74) *Attorney, Agent, or Firm* — Foster Garvey PC

(57) ABSTRACT

Described herein is a tissue retractor for use in endodontic procedures. The tissue retractor includes a bite pad having a proximal end and a distal end, a tooth registration block connected to the distal end of the bite pad, an arm having a proximal end and distal end, where the proximal end is connected to the tooth registration block such that the tooth registration block is between the bite pad and the arm, a cheek retractor having a proximal end, a distal end and a length, the length defining a top edge and a bottom edge, where the distal end of the cheek retractor is connected to the distal end of the arm, and at least one cheek catch extending from the top edge of the cheek retractor.

20 Claims, 5 Drawing Sheets

ENDODONTIC SURGERY TISSUE RETRACTOR DEVICE

CROSS-REFERENCE TO RELATED APPLICATIONS

This application claims priority to and the benefit of U.S. Provisional Application No. 63/493,017, filed Mar. 30, 2023, the disclosure of which is incorporated herein by reference in its entirety.

BACKGROUND OF THE INVENTION

Dental professionals utilize numerous different devices to retract soft oral tissue around the oral cavity so as to create an enlarged working field around the teeth and dental arches. For example, cheek retractors are used to hold the patient's mouth open so that the dental professional can have easy access to the teeth. However, because patients have different sized mouths, existing cheek retractors are often not a proper fit for certain patients, leading to significant problems with surgical site accessibility and patient discomfort. Further, existing devices are often difficult to insert and remove, and typically require extensive time to implement. In certain instances, these devices can activate patient's pharyngeal reflexes.

Thus, there is a need in the art for improved tissue retractor designs. The present invention satisfies this need.

SUMMARY OF THE INVENTION

Described herein is a tissue retractor for use in endodontic procedures. The tissue retractor includes a bite pad having a proximal end and a distal end, a tooth registration block connected to the distal end of the bite pad, an arm having a proximal end and distal end, where the proximal end is connected to the tooth registration block such that the tooth registration block is between the bite pad and the arm, a cheek retractor having a proximal end, a distal end and a length, the length defining a top edge and a bottom edge, where the distal end of the cheek retractor is connected to the distal end of the arm, and at least one cheek catch extending from the top edge of the cheek retractor. In some embodiments, the retractor includes a jawbone registration element connected to the distal end of the cheek retractor. In some embodiments, the bite pad, arm, cheek retractor and at least one cheek catch are bendable and shape-holding. In some embodiments, the arm has a shoulder region at the proximal end, such that the width of the arm decreases distally across the shoulder region. In some embodiments, the proximal end of the cheek retractor is adjacent but not in contact with the proximal shoulder region of the arm. In some embodiments, the bite pad, arm and cheek retractor have a flat profile in the same plane when unbent. In some embodiments, the tooth registration block protrudes outwardly from the plane of the bite pad, arm and cheek retractor. In some embodiments, the at least one cheek catch extends in the same plane as the cheek retractor when unbent. In some embodiments, the bite pad, tooth registration block, arm and cheek retractor are a single unit. In some embodiments, the bite pad comprises a metal core encapsulated by an exterior shell. In some embodiments, the bite pad comprises at least one frangible tab at the distal end of the bite pad. In some embodiments, the at least one frangible tab comprises a region of reduced thickness of the exterior shell. In some embodiments, the metal core includes a breaking region off-set from the exterior shell region of reduced thickness.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
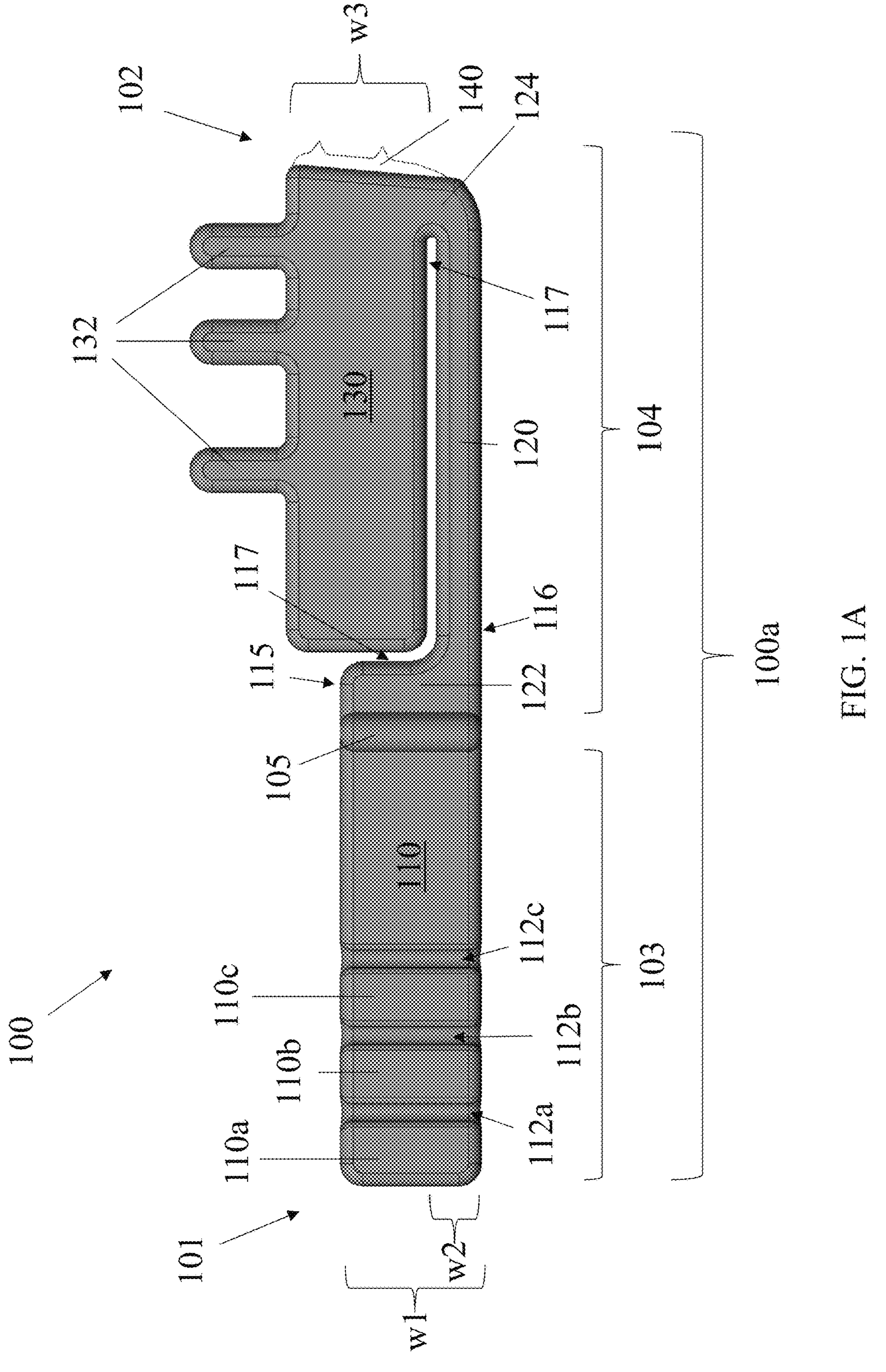
FIG. 1A is a front view of an exemplary endodontic surgery tissue retractor device.

It is to be understood that the figures and descriptions of the present invention have been simplified to illustrate elements that are relevant for a clearer comprehension of the present invention, while eliminating, for the purpose of clarity, many other elements found in endodontic tissue retractors. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views and various embodiments, is an endodontic surgery tissue retractor device.

Referring now to FIGS. 1A-1D, an exemplary endodontic surgery tissue retractor or device 100 is presented. Device 100 generally includes a body 100*a* having a proximal end 101 and a distal end 102. The total length of body 100*a* between proximal and distal ends 101 and 102 may be between 16 cm and 17.5 cm. The body 100*a* further defines a proximal region 103 and distal region 104, separated by a tooth registration block 105. All or a portion of body 100*a* may include a thin central unit 150 that is fully or partially encapsulated by an exterior shell 160. Thin central unit 150 may be a metal or any other desired material. In some embodiments, central unit 150 is bendable and shape-holding, such that body 100*a* will remain in any shape bent or folded into. In some embodiments, central unit 150 is frangible, such that it may be broken or snapped with enough applied force and/or bent or twisted significantly. Exterior shell 160 may be a rubber, soft or hard plastics, or any other desired material suitable for positioning comfortably in a patient's oral cavity. In some embodiments, exterior shell 160 should be bendable and flexible, such that body 100*a* is capable of holding any shape it is bent into.

Proximal region 103 generally includes a bite pad 110 extending proximally from tooth registration block 105. Bite pad 110 may be any desired width w1 and any desired length. In some embodiments, bite pad 110 may have a width w1 between 6 cm and 8 cm. In some embodiments, the length of bite pad 110 may be between 6 cm and 8 cm. In some embodiments, the length of bite pad 110 may be a fixed length or an adjustable length. For example, bite pad 110 may include one or more frangible tabs 110*a*-110*c* each separated by one or more break points 112*a*-112*c*. Frangible tabs 110*a-c* may each be any length desired.

Figure 1B:
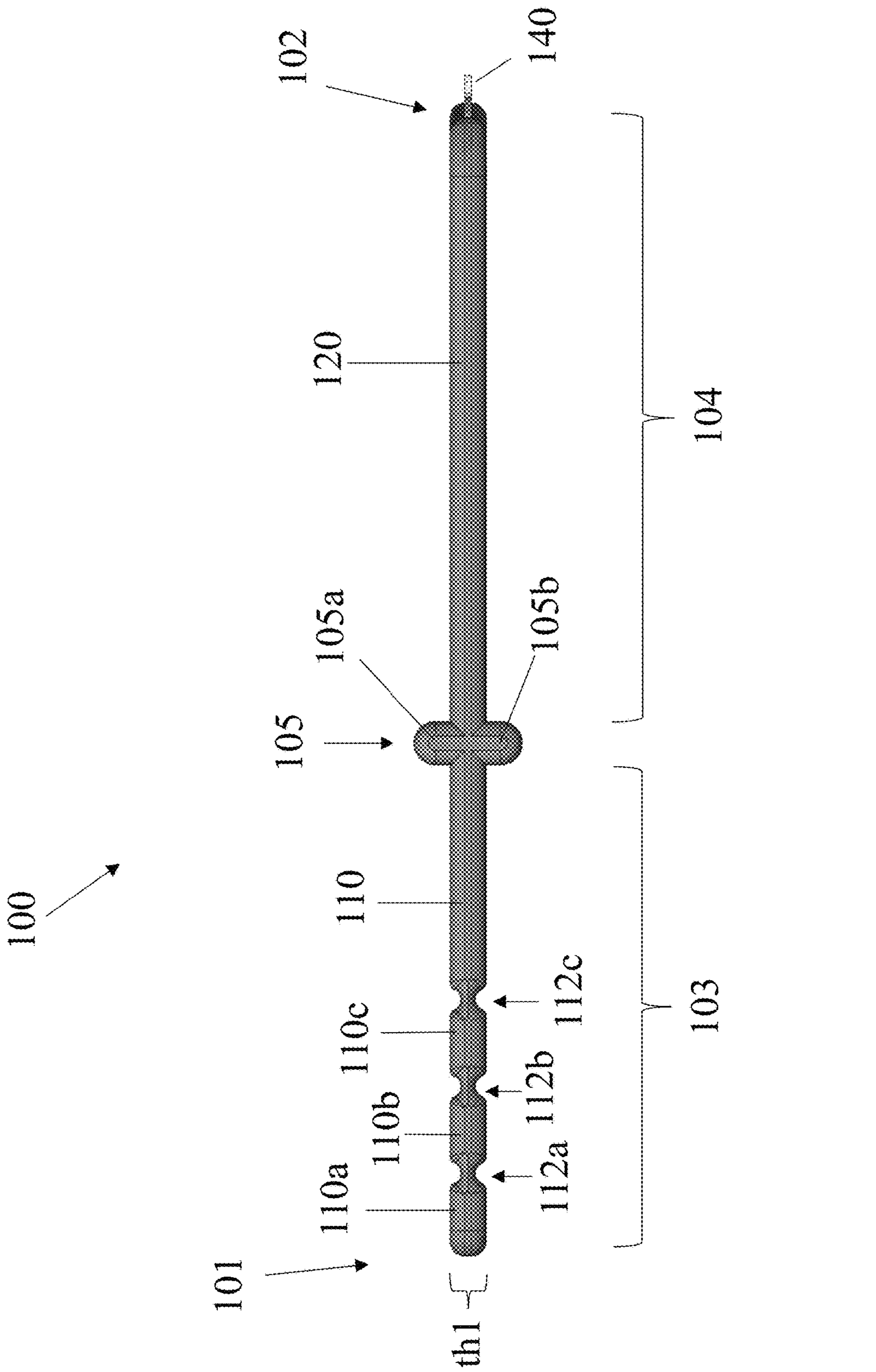
FIG. 1B is bottom view of the endodontic surgery tissue retractor device shown in FIG. 1A.
Figure 1C:
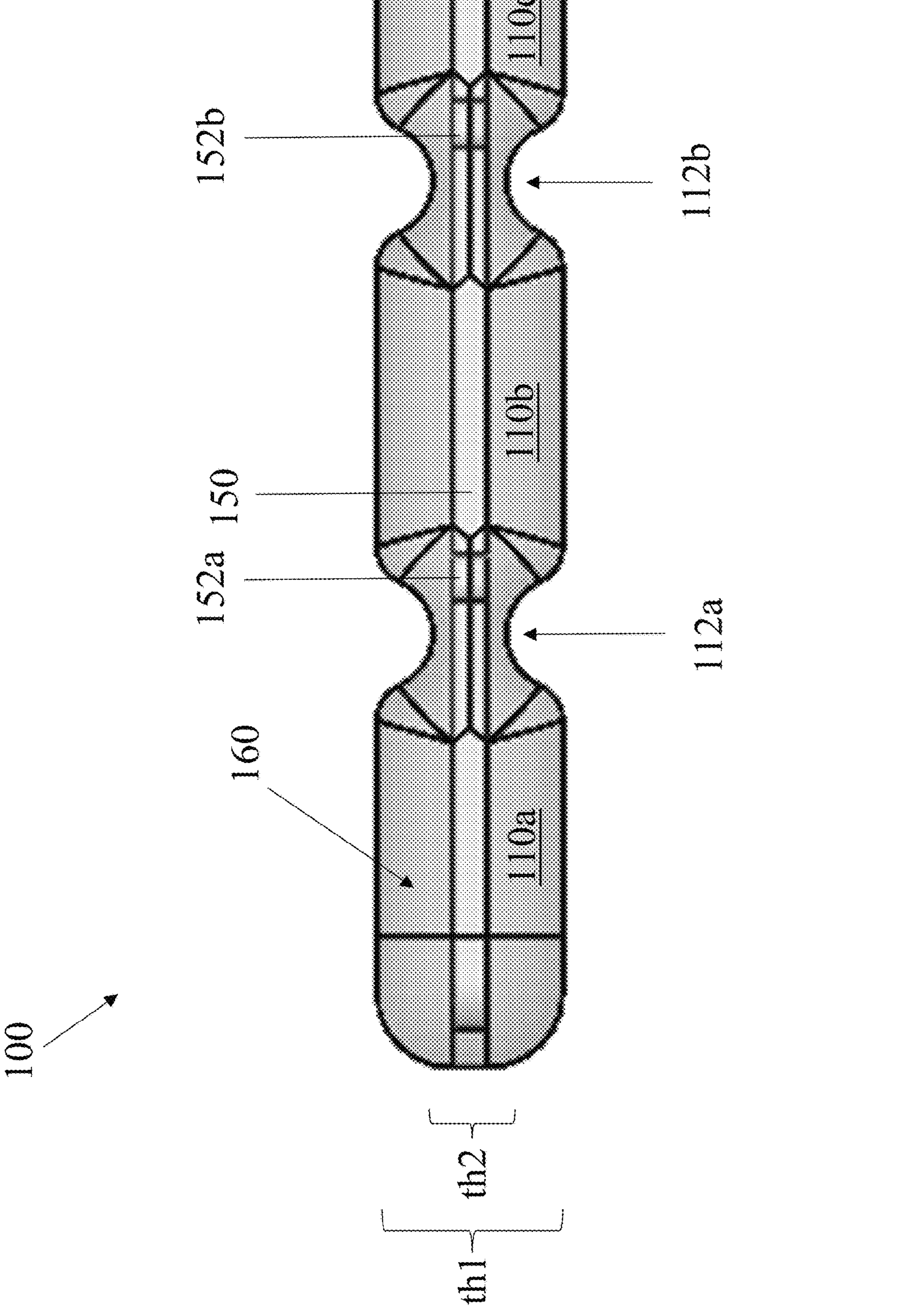
FIG. 1C is an enlarged, transparent bottom view of a portion of the endodontic surgery tissue retractor device shown in FIG. 1A.

As shown in FIG. 1C, bite pad 110 may have any thickness th1. Further, break points 112*a*-112*c* each represent a section with a reduced thickness th2 of bite pad 110, thereby forming frangible tabs 110*a*-110*c* proximal to each break point 112*a*-112*c*, respectively. In some embodiments, reduced thickness th2 may be between 30-50% the thickness of th1. While central unit 150 generally bends and holds shape along the length of body 100*a* at thickness th1, reduced thickness th2 of the exterior shell 160 permits central unit 150 and exterior shell 160 to snap and detach when bent and/or twisted at any of breaking points 112*a*-112*c*.

Figure 1D:
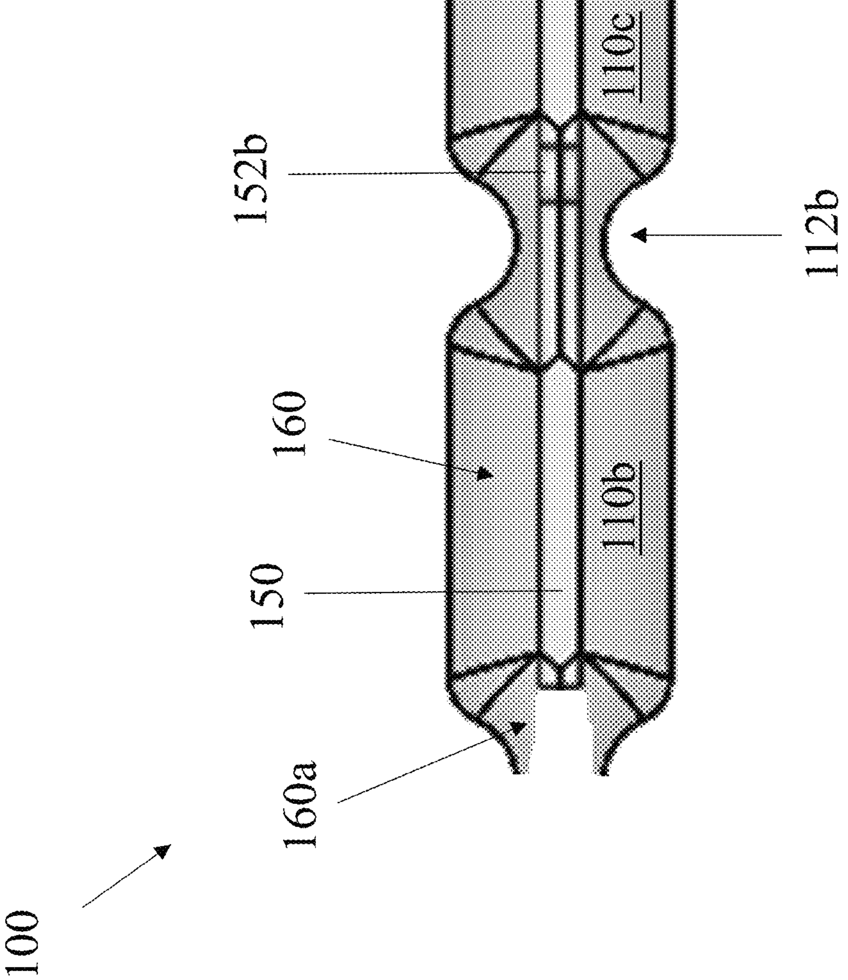
FIG. 1D is an enlarged, transparent bottom view of a portion of the endodontic surgery tissue retractor device shown in FIG. 1A with a frangible tab removed from the proximal end of the device.

In some embodiments, central unit 150 has one or more breaking points 152. Central unit breaking point 152 may be formed with perforations in central unit 150, or alternatively it may be of a reduced thickness compared to the remainder of central unit 150. In some embodiments, central unit breaking point 152 may be aligned with a breaking point 112, or it may be off-set from breaking point 112. For example, if off-set as shown in FIG. 1C, central unit 150 snaps at breaking point 152*a* while external shell 160 snaps at breaking point 112*a*, thereby allowing frangible tab 110*a* to detach from the remainder of bite pad 110 with a portion of external shell 160*a* overlapping the new proximal end of central unit 150, as shown in FIG. 1D. Accordingly, the length of bite pad 110 may be adjustably shortened by detaching one or more frangible tabs 110*a-c*.

Figure 2A:
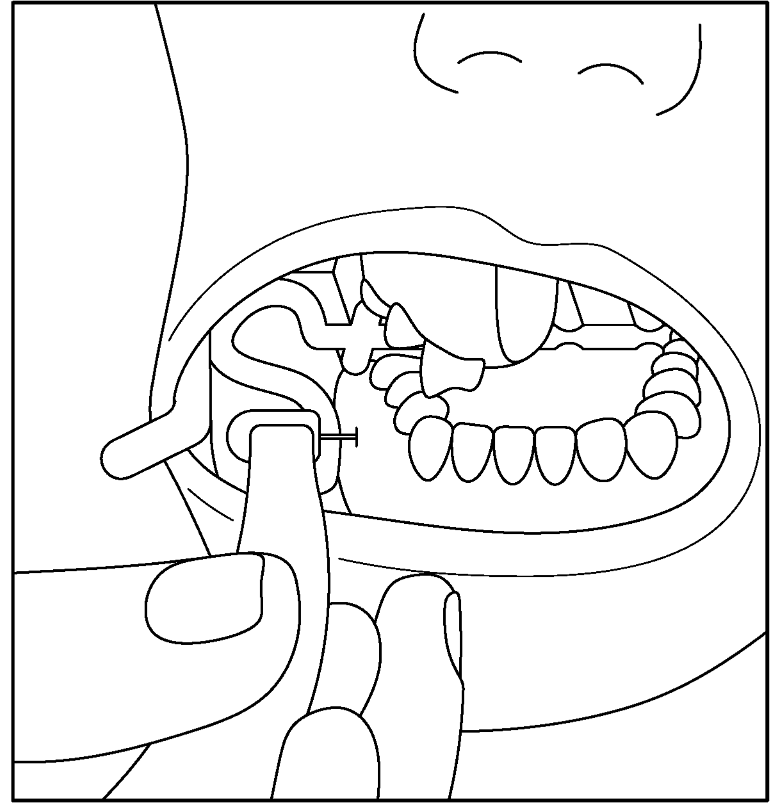
FIG. 2A and FIG. 2B are images of an exemplary endodontic surgery tissue retractor device positioned within a patient's oral cavity.
Figure 2B:
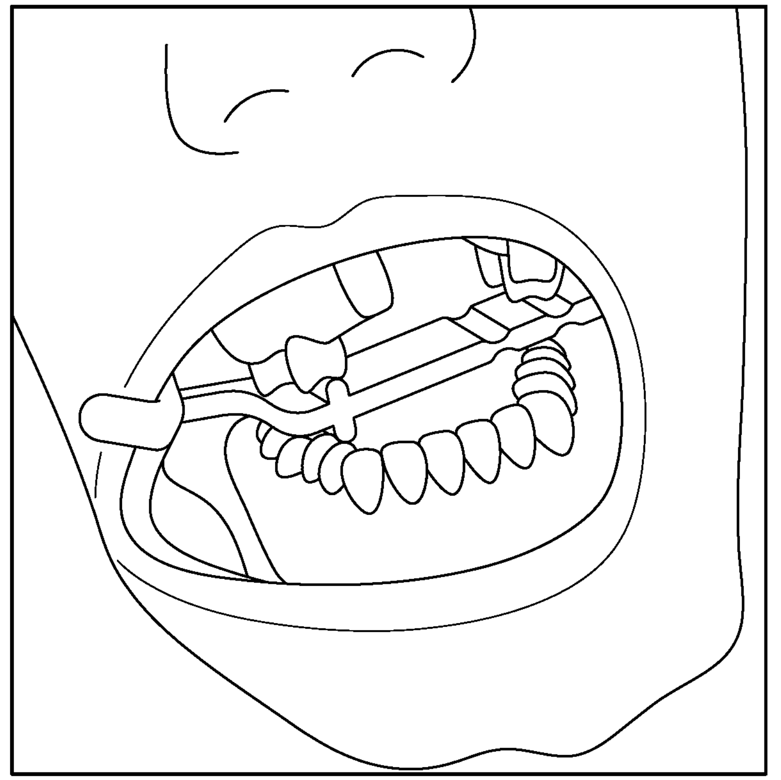

As shown in FIG. 1B, tooth registration block 105 sits between proximal region 103 and distal region 104 and includes one or more protrusions 105*a* and/or 105*b* extending outwardly from the front or back surface of device 100. Tooth registration block 105 assists in proper placement of device 100 in the oral cavity of a subject, as shown in FIGS. 2A and 2B. Protrusions 105*a* and/or 105*b* may extend any desired distance from the surface of body 100*a*. In some embodiments, protrusions 105*a* and/or 105*b* may extend between 0.5 cm and 1 cm. In some embodiments, protrusions 105*a* and/or 105*b* may be a fixed, single unit with body 100*a*, or they may be separate components that are releasably attached to body 100*a* at one or more locations along the length of body 100*a*.

Distal region 104 generally includes an arm 120 and a cheek retractor 130. Arm 120 includes a proximal shoulder region 122 transitioning from a wider material width w1 at the distal side of tooth registration block 105 to a narrower material width w2 as arm 120 extends distally away from tooth registration block 105. In some embodiments and as shown in FIG. 1A, arm 120 has a top edge 115 and a bottom edge 116 along its length. As shown, the transition from w1 to w2 occurs across the shoulder region 122. Accordingly, the bottom edge 116 remains in-line with the bottom edge of tooth registration block 105 and bite pad 110, such that top edge 115 travels closer to bottom edge 116 until it again runs parallel to bottom edge 116 at width w2. In other embodiments, both top and bottom edges 115 and 116 travel towards each other until ultimately running parallel at width w2.

The narrower width w2 portion of arm 120 allows for increased flexibility and bending. In some embodiments, arm 120 is bendable and shape-holding, such that arm 120 will remain in any shape bent or folded into. In some embodiments, arm 120 includes central unit 150 and external shell 160 as shown and described herein. In some embodiments, width w2 may be between 4 mm and 12 mm. In some embodiments, the length of arm 120 may be between 5.5 cm and 7.5 cm.

At the distal end of arm 120 is a transition region or hinge 124 connecting cheek retractor 130. Cheek retractor 130 is adjacent to arm 120 and extends proximally towards shoulder 122 of arm 120, thereby forming a gap region 117 between arm 120 and cheek retractor 130. In some embodiments, cheek retractor 130 may have a width w3, which may be between 1.7 cm and 2.7 cm. In some embodiments, cheek retractor 130 may have a length of between 5.5 cm and 7.5 cm. In some embodiments, the length of cheek retractor 130 is equal to or less than the length of arm 120. In some embodiments, cheek retractor 130 is bendable and shape-holding, such that cheek retractor 130 will remain in any shape bent or folded into. In some embodiments, cheek retractor 130 includes central unit 150 and external shell 160 as shown and described herein. It should be appreciated that only the distal end of cheek retractor 130 is connected to the distal end of arm 120 at transition region or hinge 124. Thus, the proximal end of cheek retractor 130 is nested adjacent to, but not in contact with, shoulder region 122 of arm 120 and the length of arm 120.

Cheek retractor 130 may further include a jawbone registration element 140 at the distal end of one or both of cheek retractor 130 and transition region 124 of arm 120. In some embodiments, jawbone registration element 140 is rigid and pointed, such that it is configured to engage with the gum, teeth or jawbone of a subject when positioned in the subject's oral cavity. Jawbone registration element 140 may be composed of metal or any other rigid material suitable for placing is a subject's oral cavity. Jawbone registration element 140 may include any number of engagement points, and may alternatively include any other shapes or contoured structures that promote an engagement with the subject's gum, teeth or jawbone.

Cheek retractor 130 may further include one or more cheek catch extensions 132 extending from the top edge opposite of, or furthest from, arm 120. Cheek catch extensions 132 may extend any desired length from cheek retractor 130. In some embodiments, cheek catch extensions 132 may extend between 1.5 cm and 2.5 cm. In some embodiments, each cheek catch extension 132 may be a fixed, single unit with cheek retractor 130, or they may be separate components that are releasably attached to cheek retractor 130 at one or more locations along the length of cheek retractor 130. In some embodiments, cheek catch extensions 132 are bendable and shape-holding, such that each cheek catch extension 132 will remain in any shape bent or folded into. In some embodiments, cheek catch extensions 132 include central unit 150 and external shell 160 as shown and described herein.

In some embodiments and as shown in FIG. 1B, device 100 may have the same thickness th1 for each of the bite pad 110, arm 120 and cheek retractor 130, such that device 100 has a generally flat profile other than tooth registration block 105 when in an unbent configuration. In some embodiments, one or more of the bite pad 110, arm 120 and cheek retractor 130 may have a thickness that is different from the other components.

In use and as shown in FIGS. 2A and 2B, device 100 may be positioned in any number of configurations, depending on the size of the subject's oral cavity and anatomy, and depending on the region any given procedure requires access to. For example, the bite pad is optionally adjusted in length by snapping off one or more frangible tabs, and is positioned between the teeth of the maxillary and mandibular arches. The tooth registration block is positioned such that it is adjacent to the teeth, either on the inside surface of the teeth or the outside surface of the teeth. The arm and cheek retractor are separately bent in a generally C shaped configuration, such that the jawbone registration point engages with the tissue of the jawbone region. The arm and cheek retractor portions are uniquely bendable and moldable independently of each other to promote a more customized opening of the oral cavity space. The cheek catch extensions are subsequently bent upward and outward to contain the lip and cheek of the subject. Accordingly, the device adequately creates and holds an enlarged open area of the oral cavity for a practitioner to access the teeth, gums, jawbone or any other space needed for a given procedure.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. An endodontic tissue retractor, comprising:

a bite pad having a proximal end and a distal end;

a tooth registration block connected to the distal end of the bite pad;

an arm having a proximal end and distal end, wherein the proximal end is connected to the tooth registration block such that the tooth registration block is between the bite pad and the arm;

a cheek retractor having a proximal end, a distal end and a length, the length defining a top edge and a bottom edge, wherein the distal end of the cheek retractor is connected to the distal end of the arm; and at least one cheek catch extending from the top edge of the cheek retractor, wherein the bite pad, arm and cheek retractor have a flat profile in the same plane when unbent and the tooth registration block protrudes outwardly from the plane of the bite pad, arm and cheek retractor.

2. The tissue retractor of claim 1, further comprising a jawbone registration element connected to the distal end of the cheek retractor.

3. The tissue retractor of claim 2, wherein the jawbone registration element is rigid and pointed and is configured to engage gum, teeth, or jawbone tissue of a subject.

4. The tissue retractor of claim 1, wherein the bite pad, arm, cheek retractor and at least one cheek catch are bendable and shape-holding.

5. The tissue retractor of claim 1, wherein the arm has a shoulder region at the proximal end, such that the width of the arm decreases distally across the shoulder region.

6. The tissue retractor of claim 5, wherein the proximal end of the cheek retractor is adjacent but not in contact with the proximal shoulder region of the arm.

7. The tissue retractor of claim 5, wherein the cheek retractor is adjacent to the arm and extends proximally toward the shoulder region of the arm, thereby forming a gap region between the arm and the cheek retractor.

8. The tissue retractor of claim 7, wherein only the distal end of the cheek retractor is connected to the distal end of the arm.

9. The tissue retractor of claim 1, wherein the at least one cheek catch extends in the same plane as the cheek retractor when unbent.

10. The tissue retractor of claim 1, wherein the bite pad, tooth registration block, arm and cheek retractor are a single unit.

11. The tissue retractor of claim 1, wherein the bite pad comprises a metal core encapsulated by an exterior shell.

12. The tissue retractor of claim 11, wherein the bite pad comprises at least one frangible tab at the proximal end of the bite pad.

13. The tissue retractor of claim 12, wherein the at least one frangible tab comprises a region of reduced thickness of the exterior shell.

14. The tissue retractor of claim 13, wherein the metal core includes a breaking region off-set from the exterior shell region of reduced thickness.

15. The tissue retractor of claim 13, wherein the region of reduced thickness is between 30% and 50% of the thickness of the bite pad.

16. A tissue retractor, comprising:

a bite pad;

a cheek retractor;

an arm between the bite pad and the cheek retractor; and a tooth registration block between the bite pad and the arm, wherein the bite pad, cheek retractor and arm are bendable and shape-holding, wherein the bite pad comprises a metal core encapsulated by an exterior shell, and wherein the bite pad comprises at least one frangible tab.

17. The tissue retractor of claim 16, wherein the at least one frangible tab comprises a region of reduced thickness of the exterior shell.

18. The tissue retractor of claim 17, wherein the metal core includes a breaking region off-set from the exterior shell region of reduced thickness.

19. The tissue retractor of claim 16, further comprising a jawbone registration element connected to the cheek retractor.

20. The tissue retractor of claim 16, further comprising at least one cheek catch extending from the cheek retractor.

* * * * *